(12) United States Patent
Bigus et al.

(10) Patent No.: US 6,287,291 B1
(45) Date of Patent: Sep. 11, 2001

(54) PROTECTIVE SHEATH FOR CATHETERS

(75) Inventors: Steve Bigus, San Jose; Napoleon L. Caliguiran, Half Moon Bay; Dorrie Happ, San Jose; Virgilda Torate, Freemont, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/436,019

(22) Filed: Nov. 9, 1999

(51) Int. Cl.[7] .................................................. A61M 25/00
(52) U.S. Cl. .............................................................. 604/523
(58) Field of Search ............................. 604/523, 96–104, 604/160, 264, 280, 164.06, 164.11, 164.13

(56) References Cited

U.S. PATENT DOCUMENTS 5,957,973  9/1999  Quiachon et al. .
5,980,484 * 11/1999  Ressemann et al. ................... 604/96
6,093,194   7/2000  Mikus et al. .

FOREIGN PATENT DOCUMENTS 0 943 302 A2   9/1999  (EP) .

* cited by examiner

Primary Examiner—Richard K. Seidel
Assistant Examiner—Ann Y. Lam
(74) Attorney, Agent, or Firm—Fulwider Patton Lee & Utecht, LLP

(57) ABSTRACT

A sheath is provided for covering a device on the distal end of a catheter system during the delivery of the device to an intravascular site within a patient. The sheath can be added to any delivery system prior to use and is intended to protect a deliverable device, such as an intravascular stent, from being dislodged prematurely from the catheter system or moved with respect thereto.

5 Claims, 4 Drawing Sheets

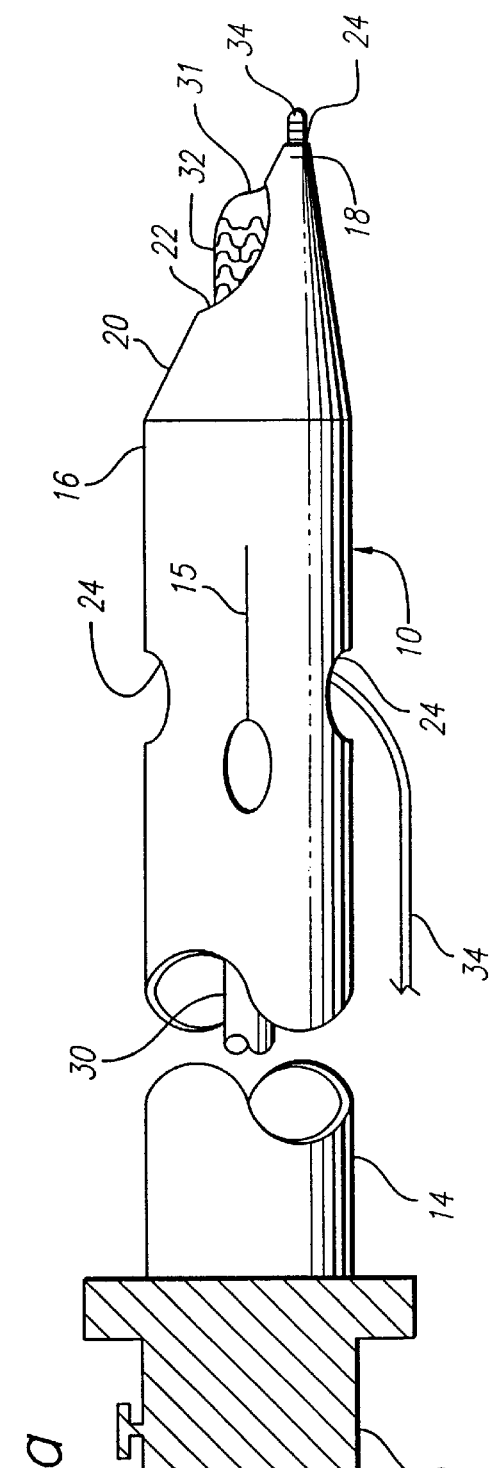
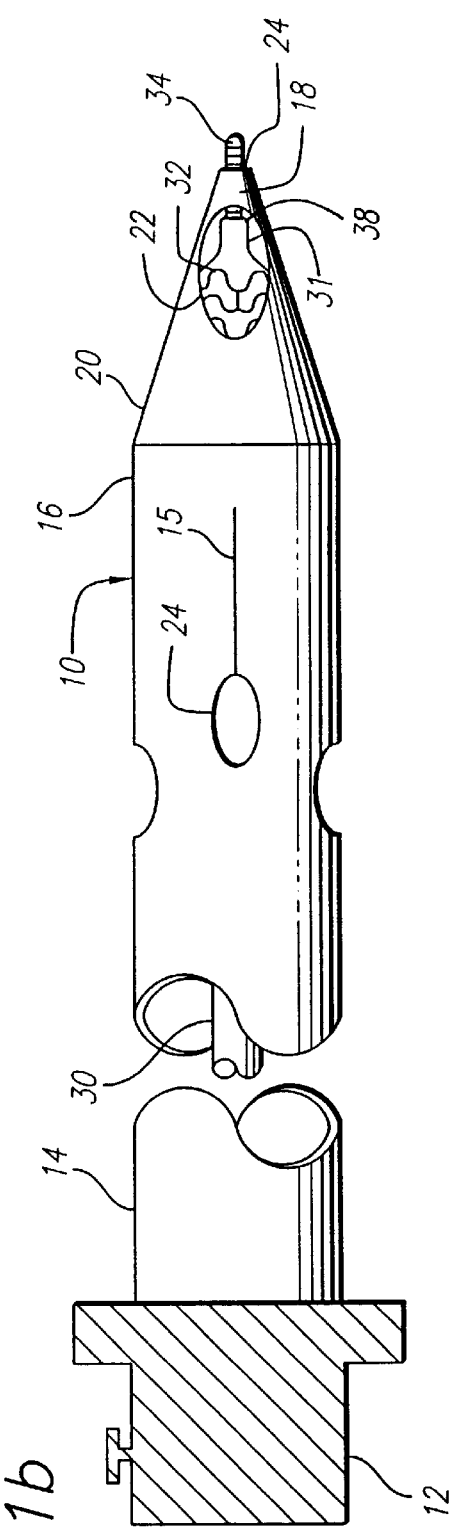
FIG. 1a
FIG. 1b

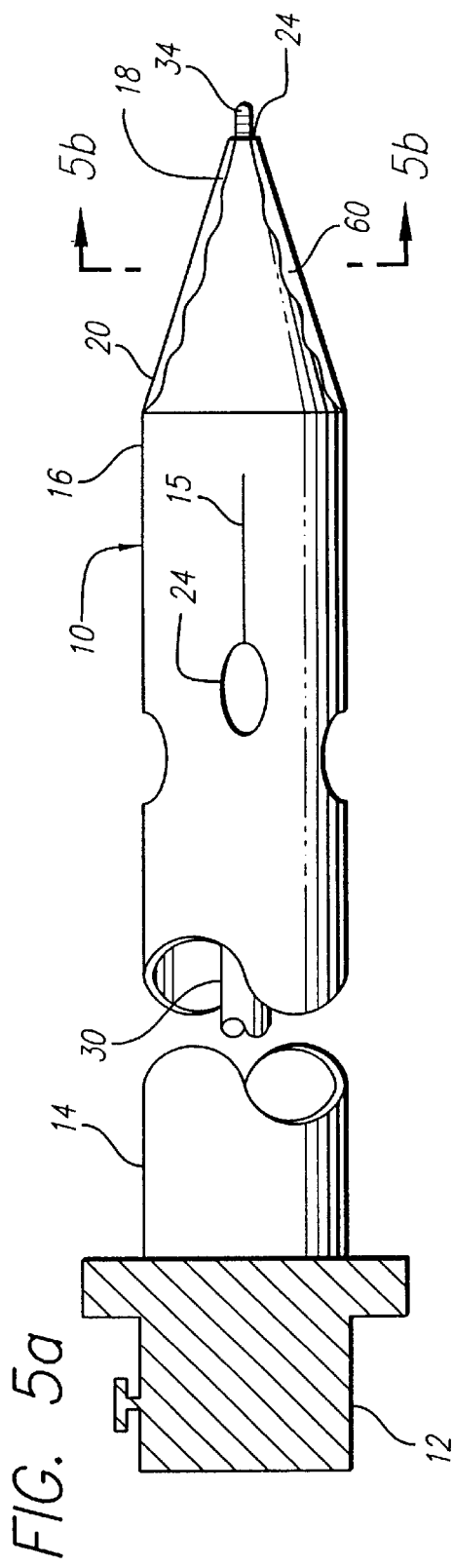
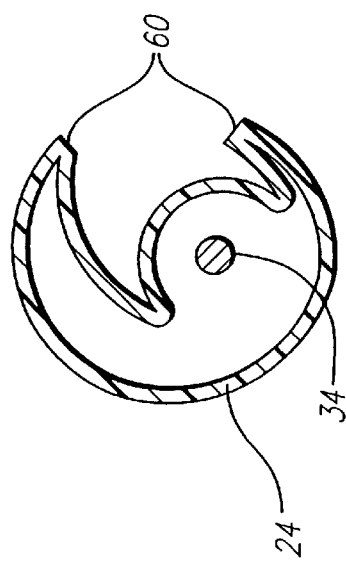
FIG. 5a
FIG. 5b

PROTECTIVE SHEATH FOR CATHETERS

BACKGROUND OF THE INVENTION

This invention is related to the use of catheter systems for treating certain conditions within the body of a patient and in particular the use of protective sheaths for covering parts of the catheter system while the system is being positioned within the patient's body.

A catheter system is used to deliver various therapeutic treatments to remote sites within a patient's body. A therapeutic device located near the distal end of the catheter system is positioned by advancing the catheter system through the tortuous curves of the patient's vasculature until the therapeutic device is in the proper position. An example of one such therapeutic device is an intravascular stent for holding open and maintaining the free passage of fluids in an artery or other vessel. A stent often may be deployed following a percutaneous transluminal coronary angioplasty (PTCA). In a PTCA procedure, a guiding catheter having a preformed distal tip is precutaneously introduced into the cardiovascular system of the patient in a conventional Seldinger technique and advanced within the cardiovascular system until the distal tip of the guiding catheter is seated at the ostium of a desired coronary artery. A guide wire is positioned within an inner lumen of a dilatation catheter having an inflatable balloon on the distal and both the catheter and guide wire are advanced through the previously placed guiding catheter to its distal end. The guide wire is first advanced out of the distal end of the guiding catheter and into the vasculature of the patient until the distal end of the guide wire crosses the lesion to be dilated. The dilatation catheter, with its distally mounted balloon, is then advanced out of the distal end of the guiding catheter over the guide wire until the balloon is properly positioned to dilate the narrowed region. The balloon is then inflated with a radiopaque fluid to a predetermined size to dilate the artery in the stenotic region. The balloon is then deflated and the catheter removed leaving the newly dilated artery with increased blood flow. In some cases the inflation of the balloon during angioplasty causes a dissection of the arterial lining or generally weakens the arterial wall in the area where the balloon was inflated. When the balloon is deflated after such a dilation, blood can flow between the arterial wall and the dissected lining, constricting the flow passage or causing a section of the lining to be forced into the flow thereby partially or completely blocking the blood flow in the artery. A stent is often used to re-secure a dissected lining in the artery wall.

Stents are well known tubular devices which, when expanded, contact the walls of a body lumen and maintains an open passage through the lumen. A stent delivery system often consists of an elongated catheter with an inflatable balloon on the distal end with an expandable stent mounted tightly around the inflatable balloon. The catheter is advanced over the in-place guide wire and then through the guiding catheter, out the distal tip of the guiding catheter and then through the patient arterial system until the stent is located at the site of the dissected arterial lining. The balloon is inflated causing the stent to expand and force the arterial lining back into place. The stent is expanded into contact with the walls of the artery at the site of the dissection and remains in an expanded state and opposed to the artery wall, holding open the artery after the balloon is deflated and the catheter and balloon are withdrawn from the patient. In an alternative procedure, an angioplasty may be performed with a stent over the dilation balloon thereby dilating the artery and ensuring its patency with a stent in one procedure.

Several problems can occur during the insertion of the stent delivery system, or any other device attached to the distal end of a delivery catheter, into the patient. One problem is that the device may become damaged on the way to the treatment site. For example, a stent may become dislodged from the balloon. This occurs when the stent bumps into the walls of the artery as it travels through the tortuous anatomy of the patient's vasculature. A second related problem is damage to the walls of the body lumen due to abrasion by the device as it passes through the vasculature. For example, a stent which often has an open lattice-like structure may present a relatively rough surface, abrading the walls of the body lumen as it passes. A third problem encountered during the insertion of the catheter system is the difficulty in advancing the leading edge of the relatively blunt end of the device such as a balloon and stent assembly past stenosed regions of the patient's arteries and ultimately past the obstruction to be repaired. This can be especially difficult in arteries with calcified deposits.

Finally, there are situations when a delivery catheter needs to be removed without first delivering the device such as when a stent cannot be delivered because of an unpassable obstruction or other complication. In this situation, the delivery catheter must be withdrawn and the stent must pass back through the distal port of the guiding catheter. There is a potential danger that the stent will become dislodged as it traverses the distal port of the guiding catheter. It may be the case that the guiding catheter must also be withdrawn if an undeployed device such as an unexpanded stent is to be removed safely.

One solution to the problem of abrasion between the device to be delivered and the walls of the body lumen is to enclose the device or the entire distal end of the device delivery system in a protective cover or sheath.

The prior art discloses catheter systems with pre-attached sheaths, which are typically incorporated onto the catheter system when the catheter is manufactured. Several examples of these types of sheath systems can be found in U.S. Pat. No. 4,733,665 to Palmaz, U.S. Pat. No. 5,458,615 to Klemm et al., and U.S. Pat. No. 5,158,548 to Lau et al.

Additional reasons for using a sheath with the delivery catheter system can include the overall poor condition of the patient's vasculature and where there is an increased risk of damage or embolism. Additionally, unexpected obstructions encountered during the dilation phase of the PTCA may, in the opinion of the physician, warrant the use of a sheath.

While there are several reasons that warrant use of a sheath to cover a device such as a stent, there also are factors which mitigate against using a sheath. One such factor is the additional time required to retract or remove the sheath from the device to be deployed. This is important when the physician wishes to minimize the time an artery is blocked by the device and where the size of the device is large relative to the size of the vessel. Another factor is that the addition of a sheath may make the overall outer diameter of the catheter too large to safely reach the treatment site. Another situation where the added complexity of using a sheath may not be warranted is when the blockage in the patient's artery is very close to the distal end of the guiding catheter so that the distance the delivery catheter must travel through the arteries is small. Here the opportunity for damage to either the device to be delivered or the walls of the patient's vasculature may be minimal.

As indicated above, some catheter systems include sheaths when they are manufactured so that the physician has no choice but to use the sheath, even if the application does not require the added protection provided by the sheath or warrant the added complexity.

What has been needed and heretofore unavailable is a sheath with a low profile to aid in catheter insertion which may be selected and added to a catheter system by the physician based on the condition encountered, thereby allowing the flexibility of using a sheath with a variety of catheter systems not originally designed to use a sheath.

SUMMARY OF THE INVENTION

This invention is directed to a protective sheath for covering a catheter delivery system which travels over a guide wire. The catheter delivery system is adapted to deliver a therapeutic device such as an intravascular stent to a position within a patient's vasculature. The design of the sheath is flexible enough to be used with a range of catheter systems not originally fitted with protective sheaths and allows the physician to retrofit a catheter to adapt to unexpected conditions.

The sheath of the present invention allows for the rapid and safe deployment of the therapeutic device within the patient's vascular system or other bodily lumen while protecting the therapeutic device from becoming prematurely dislodged or damaged and protecting the body lumen from abrasion from the therapeutic device as it passes through the body lumen. The sheath also provides a ore streamlined profile for the catheter system as it passes through the body lumen hereby reducing the effort required in inserting the device and reducing the trauma to the walls of the body lumen. The design is such that the sheath could be added to catheter systems originally designed without a sheath when the use of a sheath is warranted in the opinion of the physician. Finally, the sheath allows the withdrawal of an undelivered device back into a previously inserted guiding catheter thereby avoiding the premature removal of the guiding catheter.

The sheath is composed of an adapter, a body, a protective section, and a tip section. The adapter serves two functions. One function is to prevent back-flow of blood; the second function is to provide a port to allow flushing of the device with saline or another fluid before insertion into the patient. The body provides a means for providing translational motion of the sheath relative to the enclosed, protected, catheter. In one preferred embodiment the body is a tube. The protective section rests over the distal end area of the enclosed catheter and isolates the area from any of the forces generated during advancement to the treatment site. One unique feature of this device is the manner in which the protective section smoothly transitions to the tip section. In a preferred embodiment, a notch is formed in its entirety within a tapered outer wall surface of the reduced cross section distal end of the protective section adjacent to the distal tip between the protective section and the tip to allow the sheath to be retracted relative to the protected area, thereby exposing a therapeutic device such as a stent. This notch is formed within the surface of the tapered outer wall and is distinct and proximally placed from the distal tip. In other embodiments, the tip is shaped to closely match the profile of the therapeutic device, and may thus encompass folds, slits, or be otherwise specially shaped.

The sheath will have an inner diameter large enough to accommodate the intravascular catheter and to allow the catheter free longitudinal movement therein. In an alternate embodiment the protective section could have an inner diameter such that the protective section must be stretched slightly to enclose the device disposed on the distal end of the delivery catheter thereby providing a secure fit.

An important feature of the invention is that the sheath can be added to a catheter system based on the judgment of the physician at the time of the procedure. This allows the physician to adapt to conditions encountered during the procedure.

Another feature of the invention is that this sheath design can be used with any catheter system which uses a guide wire. Although, optimal performance should result when a sheath is matched at least in inside diameter and overall length to a particular catheter system.

An important feature of the invention is the tapered end section of the protective section. This tapered end facilitates the advancement of the catheter system by reducing the frontal area presented by the catheter as it travels through the patient's vasculature. Additionally, the sheath may be coated, such as with a silicone or a hydrophilic coating, to further reduce the effort required to advance the device through the vasculature and/or increase the ability of the device to cross a lesion or a region of stenosis. The sheath of the present invention thus allows the use of coatings that may not otherwise be desirable for use with a typical stent delivery catheter due to possible contamination of the stent by the coating substance.

The sheath may be made of a variety of materials. Most simply, a polymeric material may be used. The tubular body of the sheath need not be made of the same material as the protective section or the tip section. For example, the protective section could be made of a woven material such as fabric. Additionally, a felt or non-woven material could also be used. The material chosen for the protective section must have sufficient flexibility to allow usage of the underlying catheter in its usual manner.

The tip of the sheath can be either the same material as the protective section, or can be of entirely different construction altogether. This flexibility in design is an important feature of this invention. This flexibility allows the tip to be designed for optimal access to a lesion and crossing thereof.

The primary function of the body of the sheath is to allow for movement of the protective section relative to the enclosed catheter. The body could be as simple as an elongated member attached to the protective section and extending out of the patient's body to allow the protective section to be retracted. In the preferred embodiment, the body is a tube through which the catheter is inserted. The tube may be made from a variety of polymers or even metal. Additionally, the tube may have one or more holes (exit ports) near its distal end to allow a guide wire to pass through should the enclosed catheter be of the well-known rapid-exchange (RX) type.

In a preferred method of using the sheath with a balloon catheter containing a stent, the catheter assembly with the stent mounted thereon is inserted through the sheath adapter and advanced through the sheath until the tip of the catheter/stent abuts the tip of the sheath. A guide wire is inserted through the distal tip of the sheath and through the distal tip of the catheter. The sheath-catheter/stent assembly is advanced over the guide wire similar to a dilatation catheter. The sheath may be formed with one or more exit ports near the distal end, or alternatively with full or partial slits extending to the proximal portion, so that if a catheter/stent of the rapid-exchange (RX) type is used, the guide wire can exit through the sheath.

Once the sheath system is advanced to the treatment site, the guide wire is retracted proximally into the dilation catheter. The purpose of withdrawing the guide wire is to disengage it from the tip of the sheath. The sheath is now capable of being retracted proximally to expose the underlying stent. Once the guide wire is disengaged from the sheath tip, it is possible to re-advance the guide wire through the notch in the protective section and distally into the artery and distal of the treatment site. The relative axial position of the delivery sheath and the intravascular catheter having the stent thereon is adjusted to urge the distal end of the vascular catheter out of the notch in the protective section to expose the expandable stent. Either the catheter can be advanced distally with respect to the sheath or the sheath may be withdrawn proximally with respect to the catheter or both movements could be employed. Once the stent is completely out of the delivery sheath, the expandable member on the intravascular catheter can be expanded to expand the stent into contact with the vessel in a known manner.

While the present invention has been described herein in terms of delivering expandable stents to locations within a patient's body lumen, the sheath of this invention can be used to protect most catheters which utilize a guide wire and which are used to perform procedures involving other devices in other locations within any body lumen. Various changes and improvements may also be made to the invention without departing from the scope thereof.

BRIEF DESCRIPTION OF THE DRAWINGS

FIG. 1a is a side view depicting the preferred embodiment of the sheath with a tubular body and adapter.

FIG. 1b is a cross-sectional view of the sheath in FIG. 1a showing the notch within the tapered outer wall surface of the reduced cross-section distal end.

FIG. 5 is an elevational view depicting still another alternative embodiment of the sheath of the present invention.

DETAILED DESCRIPTION OF THE PREFERRED EMBODIMENTS

In general, the invention relates to a sheath for use with a catheter which travels over a guide wire. The sheath is designed to allow safe deployment of a therapeutic device disposed on the distal end of the delivery catheter within the vasculature or other body lumen of a patient. Specifically, the sheath is designed to protect the device from becoming prematurely dislodged or damaged, and to protect the body lumen from injury by the device as it is being inserted. The sheath provides a more streamline profile for the catheter system as it passes through the body lumen, thereby reducing the force required to insert the device and in turn reducing the trauma experienced by the walls of the body lumen. The sheath may be added to existing catheter systems when, in the opinion of the treating physician, a sheath is warranted, e.g., when attempting to navigate very tortuous vessels or when crossing extremely tight lesions. The sheath also adds a level of safety should the delivery catheter need to be withdrawn into a guiding catheter without first deploying the therapeutic device.

Figure 2:
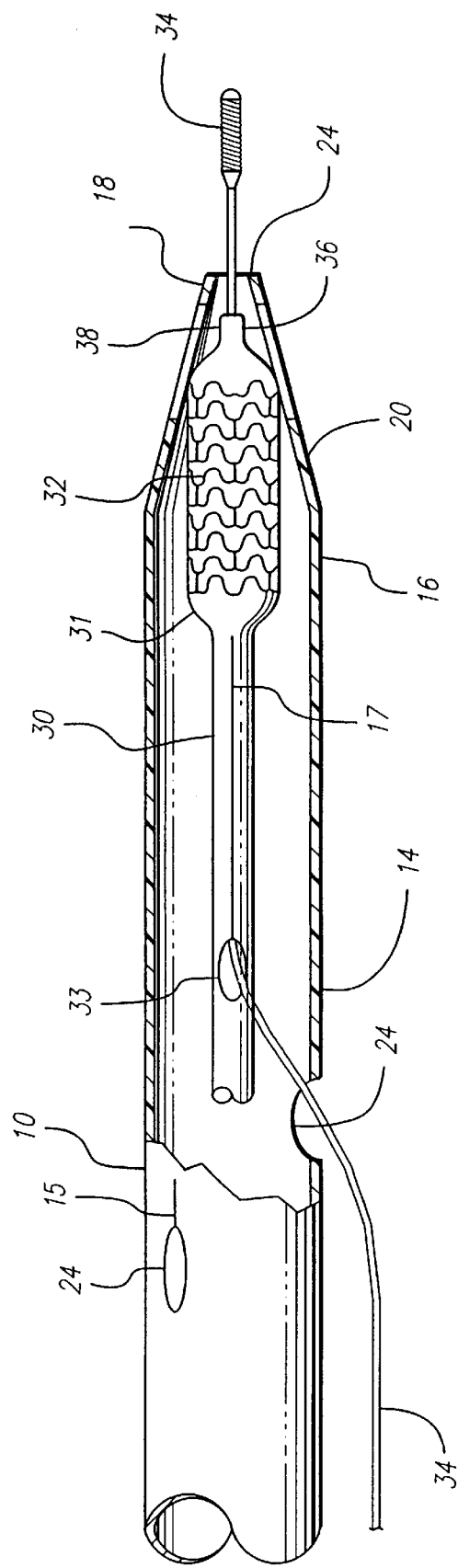
FIG. 2 is a partial cross-sectional view depicting the sheath of FIG. 1 in a fully advanced position over a delivery catheter with a stent mounted thereon.

FIGS. 1a and 1b and 2 illustrate protective sheath 10 which embodies the features of a preferred embodiment of the invention. It should be understood that all of the drawings are only exemplary and merely set an environment through which the invention may be understood. The sheath, as shown in FIGS. 1a and 1b is comprised of adapter 12, tubular body 14, protective section 16, and tip section 18. The adapter 12 serves two functions. One function is to prevent back-flow of blood; the second function is to provide a port to allow flushing of the device with saline or other fluid before insertion into the patient, a procedure that is well known. The tubular body 14 provides for transitional motion of sheath 10 relative to the catheter system, an example of which is catheter 30 shown in FIGS. 2 and 3. In one preferred embodiment, tubular body 14 is a tube and protective section 16 is positioned over distal end 36 of catheter 30 to isolate it from any of the forces generated during advancement of the catheter and sheath to the treatment site. Alternatively, tubular body 14 may be formed of a proximal section that is relatively stiffer to aid in retracting the sheath, and a distal section adjacent the protective section that is more flexible to aid in tracking over the guidewire. The distal section of the tubular body may be formed homogeneously with the protective section.

Figure 3:
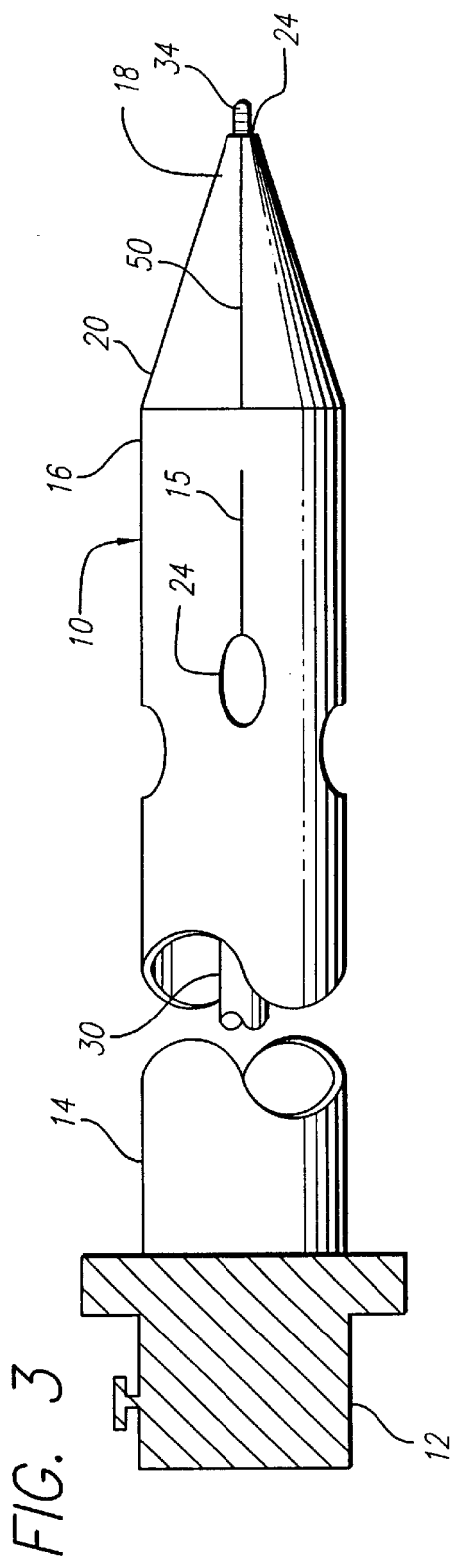
FIG. 3 is an elevational view depicting an alternative embodiment of the sheath of the present invention.

An important and unique feature of this device is the manner in which protective section 16 smoothly transitions to tip section 18 through tapered end 20. Tapered end 20 is located between the protective section and the tip and includes tapered notch 22, which allows sheath 10 to be retracted relative to an enclosed protected device (such as stent 32, as shown in FIGS. 2 and 3) thereby exposing the device (e.g. stent) and allowing it to be deployed and implanted.

In keeping with the invention, the sheath has tip 18, protective section 16, and a means for moving the protective section and tip relative to the underlying catheter system. This means for moving the protective section could include a wire or rod (not shown), however, the preferred method for moving the sheath is to provide a tubular member. If such a tubular member is used, an adapter 12 is required to prevent back-flow of blood and to allow for flushing of the device prior to insertion into the body. In situations where the catheter is of the well-known rapid-exchange type, exit port 24 near the distal end of tubular body 14 will be provided to allow guide wire 34 to exit the sheath to retain the rapid-exchange function. A slit 15 in body 14 extends distally from exit port 24 so that the guide wire can be pulled through the slit during catheter exchanges. The catheter has a corresponding slit 17 which is well known in the art.

The length of the sheath preferably is slightly shorter than the enclosed catheter system to allow independent control of the sheath and the catheter at their proximal ends. The inner diameter of the sheath must be large enough to allow the passage and relative longitudinal movement of the enclosed catheter system, but should be the smallest possible dimension to accomplish that movement in order to keep the diameter of the sheath to a minimum to ensure a low profile as the assembly is advanced through the vasculature. This is important due to extremely small diameters presented by the patient's vasculature. In an alternate embodiment, the protective section could have an inner diameter such that the protective section must be stretched slightly to enclose the device (stent) disposed on the distal end of the delivery catheter thereby providing a secure fit. This would guarantee the minimum clearance possible and could provide additional protection of the device from becoming dislodged from the distal end of the catheter.

Notch 22 in tapered end 20 of protective section 16 must be sized to allow the passage of distal end 36 of catheter system 30. This allows sheath 10 to be retracted proximally to expose the stent on distal end 36 of the catheter system and to allow the stent to be deployed.

The tapered region 20 of protective section 16 is an important feature of the invention in that it provides a lower profile to navigate the twists and bends of the vasculature than would the blunt end of the enclosed catheter as the catheter and sheath are advanced distally. This tapered profile also allows the catheter to be advanced distally of any regions of stenosis and position the stent at the implant site. In order to further increase the ability of the sheath to travel through the vasculature and through stenosed regions, all or part of the sheath may be constructed of, or coated with, a lubricating material to reduce friction between the outside of the sheath and the inside wall of the body lumen and thus further reduce the potential of damaging narrowed regions of the patient's vasculature.

Protective section 16 may be made of a variety of materials including a polymeric material, either thermoplastic or thermoset. Alternately, the protective section could be made of a woven material such as fabric like DACRON®. Additionally, a felt or non-woven material also could be used. The material chosen for protective section 16 must have sufficient flexibility to allow usage of the underlying catheter in its usual manner.

The tip of sheath 18 can be either the same material as protective section 16, or can be of entirely different construction altogether. This flexibility in design is another feature of the invention which allows the tip and tapered end sections to be designed for optimal access to a lesion and crossing thereof In one example, Primacor® (trademark of The Dow Chemical Company), an ethylene-acrylic acid copolymer, was used to fabricate the protective section. The Primacor® was then heated and necked onto a tapered mandrel to form the tip section. Primacor® was chosen because it is a low modulus material that adheres well to a wide variety of materials. In another example, the protective section was made from a polyethylene tube and was cut at an angle to form a tapered section and notch 22. The tip 18 consisted of a co-extrusion of PeBax (a trademark of ELF Atochem of France) and nylon into which had been embedded with a stainless steel coil.

As previously indicated, the means for moving the sheath 10 can include a solid mandrel. For example, a stainless steel wire (not shown) could be attached to the protective section. The wire then would extend outside the patient and it could be pulled proximally to move the protective section proximally. Improved performance is obtained, however, if tubular member 14 is coaxial to the dilation catheter 30. This means the use of a tubular member which can be any of a wide variety of polymers, or even a metallic tube.

It is anticipated that the disclosed sheath could be used in conjunction with any catheter system that also uses a guide wire. While a general use or universal sheath could be developed, it is believed that the best performance would come from a sheath that was optimized for use with a particular catheter at least in terms of inner diameter and overall length. It is also anticipated that a variety of sheaths could be developed with different materials used to construct the tip and protective section so that the physician could select the optimal characteristic of protection and flexibility necessary for a particular application.

A preferred method of using the sheath is with a balloon catheter for retaining a stent to be deployed and implanted in a vessel such as a coronary or peripheral artery. Preferably an angioplasty or atherectomy procedure is performed before the stent is implanted. When the angioplasty catheter is removed from the patient, guide wire 34 remains in position in the vessel being treated so that the lesion does not have to be re-crossed.

Catheter 30, with stent 32 mounted on expandable member 31 (generally a balloon), is inserted through sheath adapter 12 and advanced until, tip 38 of the catheter abuts the tip of sheath 18. The proximal end of guide wire 34 next is backloaded through tip 18 of the sheath and through tip 38 of the catheter. Backloading the guide wire into the distal end of the catheter is well known. The sheath/catheter combination is advanced over guide wire 34 similar to a dilatation catheter. Sheath 10 is equipped with one or more exit holes 24 so that if the catheter is of the well known rapid-exchange type, this feature will be incorporated in the sheath 10 as well. FIGS. 2 and 3 illustrate rapid-exchange catheter 30 with stent 32 inserted into the sheath 10 with a guide wire 34 extending out side port 33 of the catheter and through exit port 24 in the sheath.

Once the sheath system is advanced over the guide wire to the treatment site, the guide wire is retracted into catheter 30. The sheath is now capable of being retracted proximally to expose the underlying stent, as the catheter partially extends through notch 22 in tapered region 20 of the protective section and the guide wire no longer passes through tip section 18 of the sheath. The purpose of withdrawing guide wire 34 is to disengage it from tip 18 of the sheath which allows the sheath to be withdrawn. Once the guide wire is disengaged from sheath tip 18, it is possible and desirable to re-advance the guide wire distally in the vessel.

The relative axial position of delivery sheath 10 and catheter 30 is adjusted to urge distal end 38 of the catheter out of notch 22 in protective section 16 to expose expandable stent 32. Either catheter 30 can be advanced distally with respect to sheath 10, or, preferably, the sheath may be withdrawn proximally with respect to the catheter, or both movements could be employed.

Once the stent is completely out of the delivery sheath, expandable member 31 on the catheter is inflated to expand the stent against the vessel wall in a known manner. The sheath and catheter system is withdrawn proximally over the guide wire and removed from the patient. The guide wire may be left in the patient for follow-on procedures such as a high presence inflation balloon to firmly implant the stent.

With reference now to FIG. 3, wherein an alternative embodiment of the sheath of the present invention is depicted, tapered region 20 of sheath 10 no longer includes a notch but rather is formed with slit 50 extending longitudinally along the entire length of the tapered region from its distal end 24 to its proximal end. In use, as sheath 10 is retracted proximally, slit 50 deforms outwardly to allow catheter 30 to pass therethrough. This design does not necessitate that guidewire 34 be first retracted proximally, and can therefore be very advantageous in situations where the surgeon does not wish to retract the guidewire for fear of losing position and inability to recross the lesion. In another alternative embodiment, slit 50 can be formed to extend only partially along the length of tapered region 20 from distal end 24 to a point distal of its proximal end.

Figure 4:
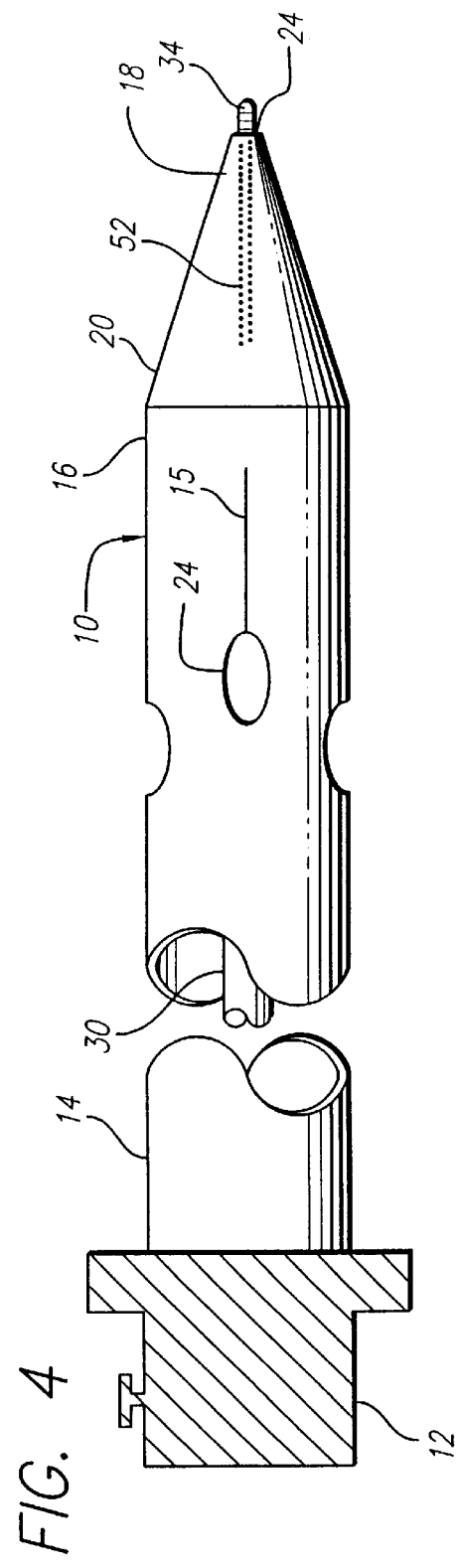
FIG. 4 is an elevational view depicting another alternative embodiment of the sheath of the present invention.

Referring now to FIG. 4, tapered portion 20 may be formed with a tear-away portion that the catheter may break through as sheath 10 is pulled proximally. This tear-away portion may be formed of perforations 52, or alternatively may be formed of a slit (such as slit 50 shown in FIG. 3) that has been heat sealed or glued back together.

FIG. 5 depicts yet another alternative embodiment, wherein tip 18 is formed in a straight tubular shape and has been folded into a tapered configuration with longitudinal folds 60. Folds 60 are heat set to retain their shape as the sheath is advanced through the vasculature, and are forced outward as the sheath is pulled proximally over the stent.

Finally, the tip could simply be shaped into a straight tubular configuration of a reduced diameter, and formed of a flexible elastomeric material that stretches as it is pulled over the catheter to allow it to pass therethrough. This embodiment would thus be similar in appearance to the embodiment depicted in FIG. 3, but would not include slit 50.

It must further be noted that although the Figures depict the various embodiments of the sheath of the present invention as providing the leading edge of the catheter and sheath assembly as the assembly is advanced through the vasculature, this is not the only configuration contemplated by the present invention. More particularly, the sheath may be formed such that the catheter tip protrudes past the sheath as the assembly is advanced through the vasculature, and the sheath encloses the catheter balloon. Alternatively, the sheath may be located even further proximally relative to the catheter, and both the catheter tip and the distal end of the catheter balloon may protrude past the sheath tip as the assembly is advanced through the vasculature.

Also included within the scope of the present invention are sheaths formed with tubular bodies of various cross sections, adapted to snugly fit over various intravascular devices. As such, a tubular body having a circular cross section is not the only embodiment contemplated by the invention. Rather, the tubular body, as well as the protective section and/or the tapered end, may be formed with various cross sections, including cross sections that vary along the length of the sheath, including, but not limited to, semi-circular, rectangular, trapezoidal, orthogonal, etc.

From the foregoing, it will be appreciated that the disclosed protective sheath is useful in protecting a device delivered on the end of a delivery catheter from becoming damaged or dislodged as it travels the tortuous paths of the patient's vasculature. The sheath additionally protects the vasculature from damage by the delivery catheter and can allow the device to be safely withdrawn without removing any guiding catheter that may be used. Finally the sheath design is flexible enough to be used with almost any delivery catheter which also uses a guide wire. While the Figures depict a rapid-exchange-style catheter, other catheters such as over-the-wire systems also would benefit from the protective sheath assembly.

While several particular forms of the invention have been illustrated and described, it will be apparent that various modifications can be made without departing from the spirit and scope of the invention. Accordingly, it is not intended that the invention be limited except as by the appended claims.

What is claimed:

1. A sheath for use with a guide wire and catheter system, comprising:

an elongated body having a distal end, wherein the elongated body is a tubular member and having an exit port closer to the distal end than to the proximal end of said elongated body through which the guide wire extends when the sheath is used with a rapid-exchange-style catheter;

a protective section for enclosing and protecting a distal portion of the catheter system, and having a proximal end adjacent the elongated body distal end and a distal end;

a tapered end section that smoothly tapers from a first larger cross section proximal end adjacent the protective section distal end to a reduced cross section distal end and being formed with a notch through which the protected enclosed distal portion of the catheter system may extend;

a distal tip disposed adjacent the tapered section reduced cross section distal end, the notch being formed entirely within a tapered outer wall surface of the reduced cross section distal end and positioned proximally relative to the distal tip; and an adapter at a proximal end of the elongated body through which the catheter system may pass, wherein said adapter is configured to prevent the back-flow of blood and allow the flushing of the sheath and catheter prior to insertion into the patient.

2. A method of protecting a catheter system with a protective sheath, the catheter system having a device on a distal end thereof, the sheath having an adapter, an elongated body, a protective region with a tapered distal end with a tapered outer wall surface containing a notch positioned proximally relative to a distal tip, and the distal tip having an exit port for a guide wire, comprising the steps of:

inserting the catheter system through the sheath adapter and advancing the catheter system until a distal tip of the catheter abuts the distal tip of the sheath;

backloading a guide wire through the distal tip of the sheath and sliding the guide wire through the distal tip of the catheter system;

advancing the protective sheath and the catheter system over the guide wire until the guide wire exits the sheath and the catheter system;

advancing the sheath and the catheter system to the treatment site within the body lumen of the patient;

retracting a distal end of the guide wire through the distal tip of the sheath and into the distal end of the catheter thereby disengaging the sheath from the guide wire;

retracting the protective sheath proximally relative to the catheter system thereby causing the distal end of the catheter containing the guide wire to pass through the notch within the tapered outer wall surface of the protective section of the sheath until the device on the distal end of the catheter is completely exposed relative to the sheath; and performing a therapeutic action using the catheter system.

3. The method of claim 2, wherein the device on the distal portion of the catheter system is a stent.

4. The method of claim 2, wherein the catheter system is of the rapid-exchange-type so that the guide wire exits the catheter at a point proximal of the device and closer to the distal end of the catheter than a proximal end of the catheter, further including the step of:

routing the guide wire through an exit port near a distal end of the elongated body of the sheath.

5. A sheath for use with a guide wire and catheter system, comprising:

an elongated body having a distal end, a protective section for enclosing and protecting a distal portion of the catheter system, and having a proximal end adjacent the elongated body distal end and a distal end;

a tapered end section that smoothly tapers from a first larger cross section proximal end adjacent the protective section distal end to a reduced cross section distal end and being formed with a notch through which the protected enclosed distal portion of the catheter system may extend, wherein the tapered section reduced cross section distal end includes a distal tip through which the guide wire may pass; and a distal tip disposed adjacent the tapered section reduced cross section distal end, the notch being formed entirely within a tapered outer wall surface of the reduced cross section distal end and positioned proximally relative to the distal tip.

* * * * *

UNITED STATES PATENT AND TRADEMARK OFFICE
CERTIFICATE OF CORRECTION

PATENT NO. : 6,287,291 B1
DATED : September 11, 2001
INVENTOR(S) : Steve Bigus et al.

It is certified that error appears in the above-identified patent and that said Letters Patent is hereby corrected as shown below:

<u>Title page,</u>
Item [56], U.S. PATENT DOCUMENTS, add the 29 U.S. Patents listed below:

| | | |
|---|---|---|
| -- 3,657,744 | 04/25/72 | Ersek |
| 4,580,568 | 04/08/86 | Gianturco |
| 4,733,665 | 03/29/88 | Palmaz |
| 4,763,654 | 08/16/88 | Jang |
| 4,921,484 | 05/01/90 | Hillstead |
| 5,002,532 | 03/26/91 | Gaiser et al. |
| 5,061,273 | 10/29/91 | Yock |
| 5,102,417 | 04/07/92 | Palmaz |
| 5,195,984 | 03/23/93 | Schatz |
| 5,226,889 | 07/13/93 | Sheiban |
| 5,454,790 | 10/03/95 | Dubrul |
| 5,456,694 | 10/10/95 | Marin et al. |
| 5,569,296 | 10/29/96 | Marin et al. |
| 5,571,086 | 11/05/96 | Kaplan |
| 5,634,928 | 01/13/97 | Fischell et al. |
| 5,643,278 | 07/01/97 | Wijay |
| 5,647,857 | 07/15/97 | Anderson et al. |
| 5,649,906 | 07/22/97 | Gory et al. |
| 5,709,701 | 01/20/98 | Parodi |
| 5,735,869 | 04/07/98 | Fernandez-Aceytuno -- |

FOREIGN PATENT DOCUMENTS, add the 10 foreign patents listed below:

| | | |
|---|---|---|
| -- EP-A-0 274 846 | 07/20/88 | European Patent Office |
| EP-A-0 479 557 | 04/08/92 | European Patent Office |
| EP-A-0 505 686 | 09/30/92 | European Patent Office |
| EP 0 540 290 A2 | 05/05/93 | EPO |
| EP-A-0 621 017 | 10/26/94 | European Patent Office |
| EP 0 637 431 A | 02/08/95 | EPO |
| EP 0 732 087 A1 | 09/18/96 | EPO |
| WO 96/33677 | 10/31/96 | WIPO |
| WO 96/39077 | 12/12/96 | PCT |
| WO 97/09932 | 03/20/97 | WIPO -- |

UNITED STATES PATENT AND TRADEMARK OFFICE
CERTIFICATE OF CORRECTION

PATENT NO. : 6,287,291 B1
DATED : September 11, 2001
INVENTOR(S) : Steve Bigus et al.

It is certified that error appears in the above-identified patent and that said Letters Patent is hereby corrected as shown below:

Item [56], add the heading -- OTHER PUBLICATIONS --, followed by the single publication listed below:

-- U.S. Application Serial No. 08/405,511, filed 3/16/95 --

Signed and Sealed this

Twenty-second Day of July, 2003

JAMES E. ROGAN
*Director of the United States Patent and Trademark Office*